(12) United States Patent
Collier, IV et al.

(10) Patent No.: US 7,329,621 B2
(45) Date of Patent: Feb. 12, 2008

(54) STRETCHABLE FILM LAMINATES AND METHODS AND APPARATUS FOR MAKING STRETCHABLE FILM LAMINATES

(75) Inventors: Leslie Warren Collier, IV, Roswell, GA (US); Susan Elaine Shawver, Roswell, GA (US); Bryon Paul Day, Canton, GA (US); Raymond Jeffrey May, Norcross, GA (US); James Russell Fitts, Jr., Gainesville, GA (US); Michael Tod Morman, Alpharetta, GA (US); Monica Varriale, Woodstock, GA (US); Matthew Boyd Lake, Cumming, GA (US); David Michael Matela, Alpharetta, GA (US); Gregory Todd Sudduth, Cumming, GA (US); Randall James Palmer, Acworth, GA (US); Charles John Morell, Roswell, GA (US); Prasad Shrikrishna Potnis, Duluth, GA (US); Rasha Wafik Zaki Guirguis, Alpharetta, GA (US); Cristian M. Neculescu, Neenah, WI (US); Peiguang Zhou, Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 165 days.

(21) Appl. No.: 10/738,644

(22) Filed: Dec. 17, 2003

(65) Prior Publication Data

US 2004/0182499 A1 Sep. 23, 2004

Related U.S. Application Data

(63) Continuation-in-part of application No. 10/330,042, filed on Dec. 26, 2002.

(51) Int. Cl.
*B32B 27/12* (2006.01)

(52) U.S. Cl. .......... 442/105; 442/50; 442/56; 442/57; 442/58; 442/65; 442/328; 442/329; 442/370; 442/373; 442/381; 442/382; 442/391; 442/392; 442/394; 442/400; 442/401; 442/409

(58) Field of Classification Search .......... 442/50, 442/56, 57, 58, 65, 105, 328, 329, 370, 373, 442/381, 382, 391, 392, 394, 400, 401, 409
See application file for complete search history.

(56) References Cited

U.S. PATENT DOCUMENTS 3,338,992 A 8/1967 Kinney (Continued)

FOREIGN PATENT DOCUMENTS

EP 0 414 917 3/1991

(Continued)

OTHER PUBLICATIONS

"Carding." McGraw-Hill Dictionary of Scientific and Technical Terms. McGraw-Hill Companies, Inc., 2003.*

(Continued)

*Primary Examiner*—Andrew T Piziali
(74) *Attorney, Agent, or Firm*—Pauley Petersen & Erickson

(57) ABSTRACT

Stretchable film laminates including a layer of elastomeric openwork, such as a plurality of elastic strands or an elastomeric mesh structure. The stretchable film laminates may include a film layer bonded to the layer of elastomeric openwork, with the film layer having cross-directional stretch and the laminate having a multi-phase stretchability profile. The stretchable film laminates may be made by extruding a film from a die, stretching the film, forming and stretching a layer of elastomeric openwork, conveying the stretched elastomeric openwork onto the film while the film is stretched, and passing the film and the elastomeric openwork through a nip. The invention also includes a machine capable of producing machine-direction, cross-direction, and biaxial stretch materials. The machine includes at least one extruder, at least one filament die and at least one film die both attached to the extruder(s), and at least one nip downstream of the extruder(s).

23 Claims, 11 Drawing Sheets

U.S. PATENT DOCUMENTS

| | | | |
|---|---|---|---|
| 3,341,394 A | | 9/1967 | Kinney |
| 3,502,538 A | | 3/1970 | Petersen |
| 3,502,763 A | | 3/1970 | Hartmann |
| 3,542,615 A | | 11/1970 | Dobo et al. |
| 3,692,618 A | | 9/1972 | Dorschner et al. |
| 3,802,817 A | | 4/1974 | Matsuki et al. |
| 3,849,241 A | | 11/1974 | Butin et al. |
| 3,904,465 A | | 9/1975 | Haase et al. |
| 3,949,128 A | | 4/1976 | Ostermeier |
| 3,973,063 A | | 8/1976 | Clayton |
| 4,285,998 A | | 8/1981 | Thibodeau |
| 4,300,562 A | | 11/1981 | Pieniak |
| 4,324,245 A | * | 4/1982 | Mesek et al. ............... 604/370 |
| 4,340,558 A | | 7/1982 | Hendrickson |
| 4,340,563 A | | 7/1982 | Appel et al. |
| 4,438,167 A | | 3/1984 | Schwarz |
| 4,522,863 A | | 6/1985 | Keck et al. |
| 4,525,407 A | | 6/1985 | Ness |
| 4,606,964 A | | 8/1986 | Wideman |
| 4,652,487 A | | 3/1987 | Morman |
| 4,661,389 A | | 4/1987 | Mudge et al. |
| 4,720,415 A | * | 1/1988 | Vander Wielen et al. ... 428/152 |
| 4,813,946 A | * | 3/1989 | Sabee .................... 604/385.27 |
| 4,908,253 A | | 3/1990 | Rasmussen |
| 4,977,011 A | | 12/1990 | Smith |
| 4,978,570 A | * | 12/1990 | Heyn et al. .................. 442/370 |
| 5,114,781 A | | 5/1992 | Morman |
| 5,116,662 A | | 5/1992 | Morman |
| 5,171,239 A | * | 12/1992 | Igaue et al. ............ 604/385.29 |
| 5,336,545 A | | 8/1994 | Morman |
| 5,364,381 A | * | 11/1994 | Soga et al. ................. 604/366 |
| 5,389,168 A | * | 2/1995 | Litchholt et al. ............. 156/77 |
| 5,514,470 A | | 5/1996 | Haffner et al. |
| 5,614,276 A | | 3/1997 | Petsetakis |
| 5,691,034 A | | 11/1997 | Krueger et al. |
| 5,707,709 A | | 1/1998 | Blake |
| 5,733,822 A | | 3/1998 | Gessner et al. |
| 5,769,993 A | | 6/1998 | Baldauf |
| 5,840,633 A | | 11/1998 | Kurihara et al. |
| 5,849,001 A | | 12/1998 | Torimae et al. |
| 5,865,926 A | * | 2/1999 | Wu et al. .................... 156/229 |
| 5,882,769 A | * | 3/1999 | McCormack et al. ....... 428/152 |
| 5,883,028 A | * | 3/1999 | Morman et al. ............ 442/394 |
| 6,066,369 A | | 5/2000 | Schulz et al. |
| 6,090,234 A | | 7/2000 | Barone et al. |
| 6,093,663 A | | 7/2000 | Ouellette et al. |
| 6,096,668 A | | 8/2000 | Abuto et al. |
| 6,169,848 B1 | | 1/2001 | Henry |
| 6,359,050 B1 | * | 3/2002 | Dohrer et al. ............... 524/425 |
| 6,365,659 B1 | | 4/2002 | Aoyama et al. |
| 6,465,073 B1 | * | 10/2002 | Morman et al. ............ 428/103 |
| 6,475,600 B1 | | 11/2002 | Morman et al. |
| 2002/0002021 A1 | | 1/2002 | May et al. |
| 2002/0009940 A1 | | 1/2002 | May et al. |
| 2002/0104608 A1 | | 8/2002 | Welch et al. |
| 2002/0138063 A1 | | 9/2002 | Kuen et al. |
| 2002/0164465 A1 | | 11/2002 | Curro et al. |

FOREIGN PATENT DOCUMENTS

| | | |
|---|---|---|
| EP | 0 676 438 | 10/1995 |
| EP | 0 803 602 A1 | 10/1997 |
| EP | 1 164 007 | 12/2001 |
| EP | 1 321 288 A2 | 6/2003 |
| WO | 91/07277 | 5/1991 |
| WO | WO 91/15365 | 10/1991 |
| WO | WO 95/29810 | 11/1995 |
| WO | 00/29199 | 5/2000 |
| WO | 01/32116 | 5/2001 |
| WO | WO 01/45927 A1 | 6/2001 |
| WO | 01/87589 | 11/2001 |
| WO | WO 01/87588 A2 | 11/2001 |
| WO | 02/34184 | 5/2002 |
| WO | 02/34511 | 5/2002 |
| WO | 02/060690 | 8/2002 |
| WO | WO 2004/005018 A1 | 1/2004 |

OTHER PUBLICATIONS

"Print." The American Heritage Dictionary of the English Language, Fourth Edition. Houghton Mifflin Company, 2004.*

* cited by examiner

STRETCHABLE FILM LAMINATES AND METHODS AND APPARATUS FOR MAKING STRETCHABLE FILM LAMINATES

This application is a continuation-in-part of U.S. patent application Ser. No. 10/330,042, filed 26 Dec. 2002. The disclosure of the prior application is incorporated herein by reference.

TECHNICAL FIELD OF THE INVENTION

This invention is directed to stretchable film laminates and methods and apparatus for making stretchable film laminates.

BACKGROUND OF THE INVENTION

Stretchable laminates are used in a number of personal care products to enable the products to conform to a wearer's body for enhanced fit and, in some cases, leakage protection. Conventional stretchable laminates typically have one layer of elastomeric material, or at most two layers of elastomeric material that are integrated upon extrusion and are not handled separately in a "green" state before being integrated into the laminate. By using only one layer of elastomeric material, or a combination of elastomeric materials each pre-formed prior to forming the stretchable laminate, the stretch capabilities of the resulting laminate are significantly limited.

One technique for enhancing the stretchability of laminates is achieved through the use of necked materials. The terms "necked" and "neck stretched" are used interchangeably to describe material, such as a nonwoven web or a laminate, that is drawn or stretched in a lengthwise direction thereby reducing its width or its transverse dimension. The controlled drawing may take place under cool temperatures, room temperature or greater temperatures and is limited to an increase in overall dimension in the direction being drawn up to the elongation required to break the material, which in many cases is about 1.2 to 1.6 times. When relaxed, the material does not return totally to its original dimensions. The necking process typically involves unwinding a sheet from a supply roll and passing it through a brake nip roll assembly driven at a given linear speed. A take-up roll or nip, operating at a linear speed higher than the brake nip roll, draws the material and generates the tension needed to elongate and neck the material.

In general, a neck bonded laminate includes an elastomeric film or filaments joined to a necked material in at least two places. The elastomeric film or filaments may be joined to the necked material at intermittent points or may be completely bonded to the necked material. The joining is accomplished while the elastic film or filaments and the necked material are in a juxtaposed configuration. The resulting neck bonded laminate is elastic in a direction generally parallel to the direction of neckdown of the necked material, and may be stretched in that direction to the breaking point of the necked material or elastic material. Neck bonded laminates are described in greater detail in U.S. Pat. No. 5,336,545 issued to Morman, which is hereby incorporated by reference in its entirety in a manner consistent with the present document.

Another type of stretchable laminate is a vertical filament laminate made using a Vertical Filament Lamination (VFL) process, which is described in PCT Publication WO01/87589, published 22 Nov. 2001, and entitled ELASTIC STRANDED LAMINATE WITH ADHESIVE BONDS AND METHOD OF MANUFACTURE by H. M. Welch et al., incorporated herein by reference. This process entails vertically extruding multiple filaments onto a quench roll, elongating the filaments, laminating the filaments to a contractible (e.g. bonded carded) web and then letting the filaments contract thus creating, for example, an elastomeric high-loft bonded carded web.

Neck bonded laminates and vertical filament laminates each have attributes distinct from one another. Namely, neck bonded laminates are cross-direction stretchable, whereas vertical filament laminates are machine-direction stretchable. It may be desirable to have the capability to manufacture both neck bonded laminates and vertical filament laminates in the same location. However, even though the same types of materials can be used to produce each of these types of laminates, different types of apparatus are required to manufacture each of these types of laminates. Thus, significant capital and material costs are expended in building and maintaining separate machines for the neck bonded laminate and the vertical filament laminate production lines.

While neck bonded laminates and vertical filament laminates are suitable for a number of uses, certain applications could benefit from stretchable laminates having additional stretch characteristics.

There is thus a need or desire for stretchable laminates having enhanced stretchability, and a method of making such stretchable laminates.

There is a further need or desire for a single machine that is capable of producing both neck bonded laminates and vertical filament laminates, as well as neck stretched bonded laminates (NSBL's) such as taught in U.S. Pat. No. 5,116,662 issued to Morman, which is hereby incorporated by reference in its entirety in a manner consistent with the present document.

SUMMARY OF THE INVENTION

The present invention is directed to stretchable laminates having enhanced stretchability, and methods of making stretchable laminates having enhanced stretchability. The invention is also directed to a machine capable of producing machine-direction, cross-direction, and biaxial stretch materials.

The stretchable laminates include at least two layers in addition to an elastomeric layer. In certain embodiments, the stretchable laminates have a multi-phase stretchability profile in the machine direction and/or in the cross direction. Examples of suitable materials for the at least two layers include necked material, elastomeric material, films, inherently extendable bicomponent spunbond and meltblown webs, or a combination of any of these materials. In one embodiment, at least two layers are necked, with one of the layers necked to a greater extent than the other. In another embodiment, one of the at least two layers can withstand greater tension without failure compared to the other layer(s). The elastomeric layer may be an elastomeric adhesive film, a plurality of elastic strands either uniformly spaced from one another or zoned, an elastomeric mesh structure, or an elastomer printed in a pattern on another layer.

The stretchable laminates may be incorporated into a garment in any suitable capacity, such as in side panels, ears, waistbands, leg elastics, and/or outer covers.

One method of making stretchable laminates includes the steps of extruding a film from a die, stretching the film, forming and stretching a layer of elastomeric openwork, conveying the stretched elastomeric openwork onto the film while the film is stretched, and passing the film and the elastomeric openwork through a nip. The film and the elastomeric openwork may be stretched to different extents. The film may be in the form of a plurality of film ribbons, a foamed elastomer, an elastomeric adhesive film, or a combination of any of these forms. The elastomeric openwork may be in the form of a plurality of elastic strands, an elastomeric mesh structure, or an elastomer printed in a pattern on a substrate. Additionally, the film and/or the elastomeric openwork may be zoned. As yet another alternative, the elastomeric openwork may be in the form of meltblown.

One or more facing layers may be laminated to the film and the elastomeric openwork. The facing layers may be necked, such as with one facing layer being necked to a greater extent than another facing layer.

The film may be passed from a first roll onto a second roll while conveying a second film from a second die onto the second roll on top of the first film and the elastomeric openwork. One or both films may be thinned, necked, and/or zoned. In certain embodiments, one or both films may be a plurality of film ribbons or a foamed elastomer. Additionally, one or more facing layers may be laminated to one or both films. The machine capable of producing machine-direction, cross-direction, and biaxial stretch materials includes at least one extruder, at least one filament die and at least one film die both attached to the extruder(s), and at least one nip downstream of the extruder(s). The machine may also include at least one unwind. The machine may further include one or more ovens upstream of the nip. Additionally, the machine may include one or more adhesive application zones upstream of the nip. In certain embodiments, the machine may include one or more rolls, such as one or more chill rolls, downstream of the film die and/or the filament die. Furthermore, the machine may also include a relaxation zone downstream of the nip or nips. The configuration of the machine is suitable for producing both neck bonded laminates and vertical filament laminates.

With the foregoing in mind, it is a feature and advantage of the invention to provide stretchable laminates having enhanced stretchability, as well as methods of making such stretchable laminates. It is another feature and advantage of the invention to provide a single machine that is capable of producing stretchable laminates including both neck bonded laminates and vertical filament laminates.

BRIEF DESCRIPTION OF THE DRAWINGS

FIGS. 11b-11d are elongation-versus-tension profiles of three of the layers within the laminate profiled in FIG. 11a.

FIGS. 12b-12d are elongation-versus-tension profiles of three of the layers within the laminate profiled in FIG. 12a.

FIGS. 13b-13d are elongation-versus-tension profiles of three of the layers within the laminate profiled in FIG. 13a.

DEFINITIONS

Figure 1:
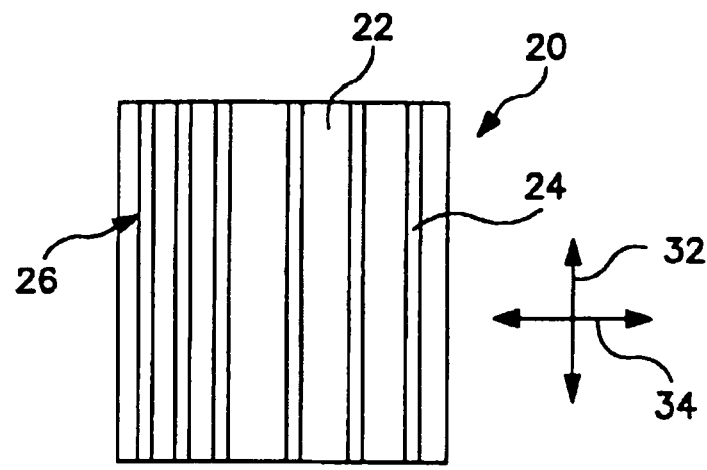
FIGS. 1-3 are plan views of various embodiments of a stretchable laminate.

Within the context of this specification, each term or phrase below will include the following meaning or meanings.

"Biaxial stretch" refers to the capability of being stretched in both the cross direction and the machine direction, and potentially any direction between the cross direction and the machine direction.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

"Elastomeric" and "elastic" are used interchangeably to refer to a material or composite that is generally capable of recovering its shape after deformation when the deforming force is removed. Specifically, as used herein, elastic or elastomeric is meant to be that property of any material which, upon application of a biasing force, permits the material to be stretchable to a stretched biased length which is at least about 50 percent greater than its relaxed unbiased length, and that will cause the material to recover at least 40 percent of its elongation upon release of the stretching force. A hypothetical example which would satisfy this definition of an elastomeric material would be a one (1) inch sample of a material which is elongatable to at least 1.50 inches and which, upon being elongated to 1.50 inches and released, will recover to a length of less than 1.30 inches. Many elastic materials may be stretched by much more than 50 percent of their relaxed length, and many of these will recover to substantially their original relaxed length upon release of the stretching force.

"Film" generally refers to a thermoplastic film made using a film extrusion process, such as a cast film or blown film extrusion process. The film could become thermoset post-extrusion using cross-linking technologies known in the industry. The term includes apertured films, slit films, and other porous films which constitute liquid transfer films, as well as microporous films which do not transfer liquid, but may transfer water vapor or other gases.

"Garment" includes personal care garments, medical garments, and the like. The term "disposable garment" includes garments which are typically disposed of after 1-5 uses. The term "personal care garment" includes diapers, training pants, swim wear, absorbent underpants, adult incontinence products, feminine hygiene products, and the like. The term "medical garment" includes medical (i.e., protective and/or surgical) gowns, caps, gloves, drapes, face masks, and the like. The term "industrial workwear garment" includes laboratory coats, cover-alls, and the like.

"Layer" when used in the singular can have the dual meaning of a single element or a plurality of elements.

"Machine direction" as applied to a film or nonwoven machine, refers to the direction on the film or nonwoven that was parallel to the direction of travel of the film or nonwoven as it left the extrusion or forming apparatus. If the film or nonwoven passed between nip rollers or chill rollers, for instance, the machine direction is the direction on the film or nonwoven that was parallel to the surface movement of the rollers when in contact with the film or nonwoven. "Cross direction" refers to the direction perpendicular to the machine direction. Dimensions measured in the cross direction are referred to as "width" dimensions, while dimensions measured in the machine direction are referred to as "length" dimensions.

"Meltblown fiber" refers to fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al., which is incorporated herein in its entirety by reference. Meltblown fibers are microfibers which may be continuous or discontinuous, are generally smaller than about 0.6 denier, and are generally self bonding when deposited onto a collecting surface.

"Mesh structure" refers to a type of openwork structure made up of entangled or overlapping strands, or a continuous layer, in which discrete openings between the top and bottom surfaces of the structure are present either in a uniform or non-uniform pattern.

"Necked material" refers to any material which has been drawn in at least one dimension, (e.g. lengthwise), reducing the transverse dimension, (e.g. width), such that when the drawing force is removed, the material can be pulled back to its original width. The necked material generally has a higher basis weight per unit area than the un-necked material. When the necked material is pulled back to its original width, it should have about the same basis weight as the un-necked material. This differs from stretching/orienting the film layer, during which the film is thinned and the basis weight is reduced.

"Nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Openwork" refers to a layer having visible openings between the top and bottom surfaces of the layer, such as a layer of parallel strands, or a mesh layer, or the like.

"Ribbon" refers to a strip of film having a width comparable to a thread, fiber, filament, cable, rope, yarn, cord, or the like.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced as taught, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10. Spunbond fibers may be monofilaments or multi-component such as in the case of bicomponent spunbond fibers with a side-by-side or sheath-core configuration, or islands-in-the-sea configuration as a multi-component example.

"Strand" refers to an article of manufacture whose width is comparable to a thread, fiber, filament, cable, rope, yarn, cord, or the like.

"Stretchable" or "extendable" means that a material can be stretched, without breaking, by at least 30% (to at least 130% of its initial (unstretched) length) in at least one direction, suitably by at least 50% (to at least 150% of its initial length), or by at least 100% (to at least 200% of its initial length). The term includes elastic materials as well as materials that stretch but do not significantly retract. A hypothetical example which would satisfy this definition of an extendable material would be a one (1) inch sample of a material which is elongatable by at least 30% to at least 1.30 inches.

"Stretch-to-stop" refers to a ratio determined from the difference between the unextended dimension of a stretchable laminate and the maximum extended dimension of a stretchable laminate upon the application of a specified tensioning force and dividing that difference by the unextended dimension of the stretchable laminate. If the stretch-to-stop is expressed in percent, this ratio is multiplied by 100. For example, a stretchable laminate having an unextended length of 5 inches (12.7 cm) and a maximum extended length of 10 inches (25.4 cm) upon applying a force of 2000 grams has a stretch-to-stop (at 2000 grams) of 100 percent. Stretch-to-stop may also be referred to as "maximum non-destructive elongation." Maximum non-destructive elongation would apply in the case of a material that has more than one perceived stretch-to-stop due to its construction. Unless specified otherwise, stretch-to-stop values are reported herein at a load of 2000 grams. In the case of more than one perceived stretch-to-stop, the load of the stretch-to-stop or maximum non-destructive elongation value may occur at less than 2000 grams. In the elongation or stretch-to-stop test, a 3-inch by 7-inch (7.62 cm by 17.78 cm) sample, with the larger dimension being the machine direction, the cross direction, or any direction in between, is placed in the jaws of a Sintech machine using a gap of 5 cm between the jaws. The sample is then pulled to a stop load of 2000 gms with a crosshead speed of about 20 inches/minute (50.8 cm/minute).

"Upstream" refers to a point in a process closer to the beginning of the process relative to the point of comparison. Conversely, "downstream" refers to a point in a process closer to the end of the process relative to the point of comparison.

"Zoned" refers to a non-uniform application, such as non-uniform spacing between strands or ribbons, or non-uniform extrusion, heat-treatment, stretching, or the like.

These terms may be defined with additional language in the remaining portions of the specification.

DETAILED DESCRIPTION OF THE PRESENTLY PREFERRED EMBODIMENTS

The present invention is directed to stretchable laminates having enhanced stretchability, as well as methods of making such stretchable laminates. The invention is also directed to a machine that is capable of producing stretchable laminates including both neck bonded laminates and vertical filament laminates.

The stretchable laminates can be incorporated into any suitable article, such as personal care garments, medical garments, and industrial workwear garments. More particularly, the stretchable laminates are suitable for use in diapers, training pants, swim wear, absorbent underpants, adult incontinence products, feminine hygiene products, protective medical gowns, surgical medical gowns, caps, gloves, drapes, face masks, laboratory coats, coveralls, and the like.

A number of elastomeric components are known for use in the design and manufacture of such articles. For example, disposable absorbent articles are known to contain elasticized leg cuffs, elasticized containment flaps, elasticized waist portions, and elasticized fastening tabs. The stretchable laminates of this invention may be applied to any suitable article to form such elasticized areas.

As shown in FIG. 1, a stretchable laminate 20 of the invention includes a film layer 22, and a layer of elastomeric openwork 24 bonded to the film layer 22. The laminate 20 is stretchable, and may also be elastomeric. The laminate 20 may have different stretch properties in the machine direction than in the cross direction. Arrows 32 and 34 in FIG. 1 depict the machine direction and the cross direction, respectively.

Figure 2:
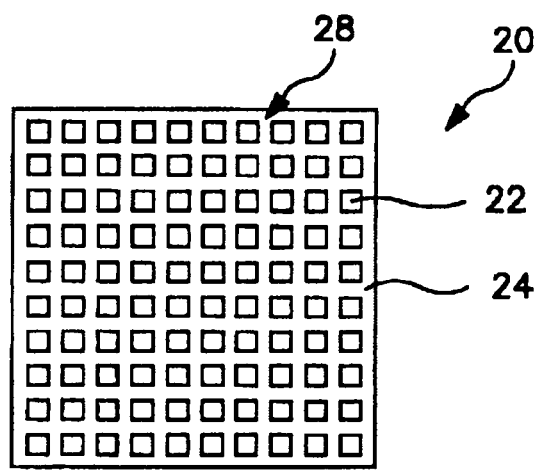
Figure 3:
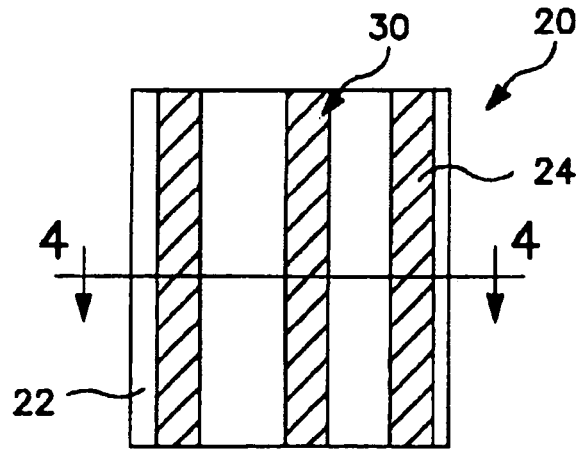

The elastomeric openwork 24 may be a plurality of elastic strands 26 (FIG. 1), an elastomeric mesh structure 28 (FIG. 2), an elastomer 30 printed in a pattern on the film layer 22 (FIG. 3), or a combination of any of these forms of elastomers. It will be appreciated that the elastomeric openwork 24 may be zoned, namely arranged periodically, non-periodically, or in various spacings, groupings, or sizes, according to the effect desired from the stretchable laminate 20 and the use to which it is put.

As shown in FIG. 1, for example, a group of strands 26 in one region of the laminate 20 can be spaced apart much more closely than another group of strands 26, resulting in greater tension in the region in which the strands 26 are more closely spaced. The strands 26 are substantially continuous in length. As another example, the elastic strands 26 may be unequally sized with some strands 26 having a larger diameter, and thus higher tension, than others. While referred to as being of different diameter, it will be appreciated that the strands 26 need not be circular in cross-section within the context of this invention. The strands 26 may have a circular cross-section, but may alternatively have other cross-sectional geometries such as elliptical, rectangular, triangular or multi-lobal. Furthermore, the strands 26 of different size or composition may be intermingled within groupings in regular or irregular patterns.

Similarly, the elastomeric openwork 24 in the form of an elastomeric mesh structure 28 or printed elastomer 30 may also be zoned, such as with a greater thickness or higher basis weight in one or more regions of the laminate 20. Suitably, the elastomeric mesh structure 28 has an overall length and width substantially equal to a length and a width of the film layer 22. The printed elastomer 30 may be any suitable pattern, such as stripes or zig-zag lines.

Materials suitable for use in preparing the elastomeric openwork 24 include raw polymers, a mixture of polymers which are also known as "compounds," as well as tackified polymers or compounds. More specifically, the elastomeric openwork 24 may include diblock, triblock, tetrablock, or other multi-block elastomeric copolymers such as olefinic copolymers, including ethylene-propylene-diene monomer (EPDM), styrene-isoprene-styrene (SIS), styrene-butadiene-styrene (SBS), styrene-ethylene/butylene-styrene (SEBS), or styrene-ethylene/propylene-styrene (SEPS), or compounds of these elastomeric copolymers, which may be obtained from the Kraton Polymers of Houston, Tex., under the trade designation KRATON® elastomeric resin, or from Dexco, a division of Exxon-Mobil, under the trade designation VECTOR® (SIS polymers); polyurethanes, including those available from E. I. Du Pont de Nemours Co., under the trade name LYCRA® polyurethane; polyamides, including polyether block amides available from Ato Chemical Company, under the trade name PEBAX® polyether block amide; polyesters, such as those available from E. I. Du Pont de Nemours Co., under the trade name HYTREL® polyester; polyisoprene; cross-linked polybutadiene; and single-site or metallocene-catalyzed polyolefins having density less than about 0.89 grams/cubic centimeter, available from Dow Chemical Co. under the trade name AFFINITY®, or a similar material available from ExxonMobil Corporation under the trade name EXACT™.

A number of other block copolymers and compounds of these copolymers can also be used to prepare the elastomeric openwork 24. Such block copolymers generally include an elastomeric midblock portion B and a thermoplastic endblock portion A. The block copolymers may also be thermoplastic in the sense that they can be melted, formed, and resolidified several times with little or no change in physical properties (assuming a minimum of oxidative degradation). Alternatively, the elastomeric openwork 24 can be made of a polymer that is not thermally processable, such as LYCRA® spandex, available from E. I. Du Pont de Nemours Co., or cross-linked natural rubber in film or fiber form. Thermoset polymers and polymers such as spandex, unlike the thermoplastic polymers, once cross-linked cannot be thermally processed, but can be obtained on a spool or other form and can be stretched and applied as strands in the same manner as thermoplastic polymers.

Endblock portion A may include a poly(vinylarene), such as polystyrene. Midblock portion B may include a substantially amorphous polyolefin such as polyisoprene, ethylene/propylene polymers, ethylene/butylenes polymers, polybutadiene, and the like, or mixtures thereof.

Suitable block copolymers may include at least two substantially polystyrene endblock portions and at least one substantially ethylene/butylene mid-block portion. A commercially available example of such a linear block copolymer is available from Kraton Polymers under the trade designation KRATON® G1657 elastomeric resin. A suitable elastomeric compounded resin is KRATON® G2760.

The film layer 22 is suitably stretchable, and may also be elastomeric. In certain embodiments, the film layer 22 may be necked for enhanced cross-directional stretch. The film layer 22 may also be breathable, such that the film layer 22 is liquid-impermeable yet is water-vapor transmissible. The film layer 22 may be filled with calcium carbonate or other suitable filler to provide enhanced breathability upon stretching. Alternatively, the film layer 22 may be a monolithic film having a basis weight of about 8 gsm or lower, or about 6 to 100 gsm.

Because the film layer 22 is bonded to the elastomeric openwork 24, the film layer 22 can be formulated to meet a sufficient level of breathability and stretchability without the additional burden of being elastic, thereby essentially decoupling elastic and breathability requirements for the film layer 22.

In general, the film layer 22 can be made from any suitable film-forming resins or blends. For example, the film layer 22 can be made from elastomeric film, foamed elastomers, or any of the materials from which the elastomeric openwork 24 can be made. The film layer 22 may also be a multilayer material in that it may include two or more individual coherent webs or films. Additionally, the film layer 22 may be a multilayer material in which one or more of the layers contain a mixture of elastic or extendable fibers or particulates.

Cross-machine-directional stretchability of the film layer 22 can be enhanced by giving the formed film layer 22 a cross-directional stretch prior to laminating the film layer 22 to the elastomeric openwork 24. A cross-directional stretch can be carried out using a tenter frame, grooved rolls, or any other technique known to those skilled in the art. Another suitable method for obtaining a cross-directional stretch of the film layer 22 is to use a blown film process that produces a film layer 22 with inherent cross-directional stretch or extendable properties. Alternatively, the film layer 22 can be stretched in the machine direction, and thereby necked, prior to lamination to the elastomeric openwork 24. By enhancing the stretchability of the film layer 22, the resulting laminate 20 may be a biaxial-stretch laminate having stretchability in both the machine direction and the cross direction.

In certain embodiments, the film layer 22 may include an elastomeric adhesive film. Suitable elastomeric, hot melt, pressure-sensitive adhesives from which the elastomeric adhesive film may be made include elastomeric polymers, tackifying resins, plasticizers, oils and antioxidants. An example of a suitable elastomeric adhesive film may be made up of 35 wt % PICOLYTE S115 and 65 wt % KRATON G2760. The elastomeric, hot melt, pressure-sensitive adhesive may be applied to a chill roll or similar device, in the form of a sheet or ribbon. The sheet or ribbon is then minimally stretched and thinned to form the film layer 22. The elastomeric adhesive film is capable not only of introducing a degree of elasticity to the stretchable laminate 20 but is also capable of providing a construction adhesive function. That is, the elastomeric adhesive film adheres itself to the elastomeric openwork 24 and/or to other components with which the elastomeric adhesive film is in contact.

One particular formulation of an elastomeric adhesive film includes a base polymer and a tackifier resin. The composition may also include additional additives. The choice of polymer and tackifier is important, as is the ratio of polymer or copolymers to tackifier. Another important consideration is the ratio of additives to tackifier.

The base polymer suitably has a styrene content of between about 15% and about 45%, or between about 18% and about 30%, by weight of the base polymer. The base polymer may achieve the styrene content either by blending different polymers having different styrene co-monomer levels or by including a single base polymer that has the desired styrene co-monomer level. Generally, the higher the styrene co-monomer level is, the higher the tension is.

The base polymer may include polystyrene-polyethylene-polypropylene-polystyrene (SEPS) block copolymer, styrene-isoprene-styrene (SIS), styrene-butadiene-styrene (SBS) block copolymer, as well as combinations of any of these. One example of a suitable SEPSEP copolymer compound is available from Kraton Polymers of Houston, Tex., under the trade designation KRATON® G 2760. One example of a suitable SIS copolymer is available from Dexco, a division of Exxon-Mobil, under the trade designation VECTOR™. Suitably, the elastomeric adhesive film composition includes the base polymer in an amount between about 30% and about 65% by weight of the composition.

The tackifier may include hydrocarbons from petroleum distillates, rosin, rosin esters, polyterpenes derived from wood, polyterpenes derived from synthetic chemicals, as well as combinations of any of these. A key element of the elastomeric adhesive film composition is a tackifier. An example of a suitable tackifier is available from Hercules Inc. of Wilmington, Del., under the trade designation PICOLYTE™ S115. Suitably, the composition includes the tackifier in an amount between about 30% and about 70% by weight of the composition.

Other additives may be included in the elastomeric adhesive film composition as well. In addition to the adhesion provided by the tackifier, various additives may provide instantaneous surface tackiness and pressure sensitive characteristics as well as reduced melt viscosity. One example of a particularly suitable low softening point additive is PICOLYTE™ S25 tackifier, available from Hercules Inc., having a softening point in a range around 25 degrees Celsius, or paraffin wax having a melting point of about 65 degrees Celsius may also be used.

Additionally, an antioxidant may be included in the elastomeric adhesive film composition, suitably in an amount between about 0.1% and about 1.0% by weight of the composition. One example of a suitable antioxidant is available from Ciba Specialty Chemicals under the trade designation IRGANOX™ 1010.

The film layer 22 suitably has a thickness of about 0.001 inch (0.025 mm) to about 0.05 inch (1.27 mm), alternatively of from about 0.001 inch (0.025 mm) to about 0.01 inch (0.25 mm).

Figure 4:
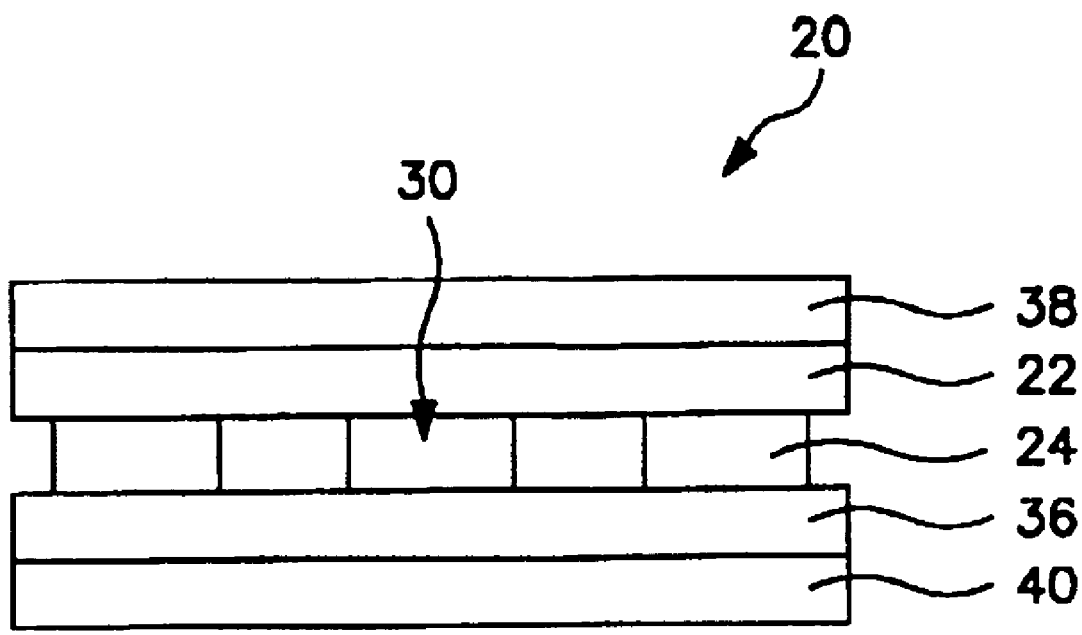
FIG. 4 is an enlarged cross-sectional view, taken along line 4-4 of FIG. 3, of another embodiment of a stretchable laminate.

As shown in FIG. 4, the stretchable laminate 20 may include multiple film layers, such as a second film layer 36 laminated to the film layer 22 with the layer of elastomeric openwork 24 positioned between the two film layers 22, 36. The second film layer 36 may be formed of the same material as the film layer 22, or may be formed of any other suitable film material, and may be either continuous or discontinuous such as in the form of a plurality of film ribbons. In certain embodiments wherein the second film layer 36 is in the form of a plurality of film ribbons, the film ribbons may be zoned to create areas of higher or lower tension, for example.

If the two film layers 22, 36 do not fully marry, or bond to one another across the entire contact surface, gaps are formed which may serve as a built-in spacer layer. Alternatively, the film layers 22, 36 can be treated with a humectant such as silica gel, a desiccant such as calcium chloride, or a water-vapor-absorbing coating or particles of superabsorbent material, on the surfaces in contact with the elastomeric openwork 24 to minimize water-vapor transfer through the laminate 20, thereby potentially reducing or eliminating dampness concerns at high breathability levels.

As shown in FIG. 4, the stretchable laminate 20 may also include one or more facing layers 38, 40 bonded to the first and/or second film layers 22, 36. Examples of suitable facing layers 38, 40 include films, nonwoven webs, such as spunbond webs and meltblown webs, or any combination thereof. In one embodiment, the facing layer 38 may be a multi-layer material having, for example, at least one layer of spunbonded web joined to at least one layer of meltblown web, or other suitable material. As another example, the facing layer 38 may be a multi-layer material having a first layer of spunbonded polypropylene having a basis weight from about 0.2 to about 8 ounces per square yard (osy), a layer of meltblown polypropylene having a basis weight from about 0.2 to about 4 osy, and a second layer of spunbonded polypropylene having a basis weight of about 0.2 to about 8 osy. Alternatively, the facing layer 38 may be a single layer of material such as, for example, a spunbonded web having a basis weight of from about 0.2 to about 10 osy or a meltblown web having a basis weight of from about 0.2 to about 8 osy. Conventional bonding techniques, such as thermal bonding, hydroentangling, and ultrasonic bonding, can be used to form the facing layer 38, as well as to bond any of the components of the laminate 20 to one another.

When two or more facing layers 38, 40 are present in the laminate 20, the facing layers 38, 40 can be the same as one another, or the facing layers 38, 40 may differ. For example, each facing layer 38, 40 may be made up of the same or different types of filaments, with the same or different types of bond patterns such as one bond pattern that provides strength and another bond pattern that provides softness. Furthermore, the facing layers 38, 40 may differ in terms of different polymers, basis weights, fiber size, fiber type, shape, and the like. Optionally, different widths of facing layers 38, 40 can be formed and necked different amounts to end up with the same width of facing layers 38, 40. The more highly necked facing layer generally will be softened more and may be weaker than the facing layer that is not necked to as great an extent.

Figure 5:
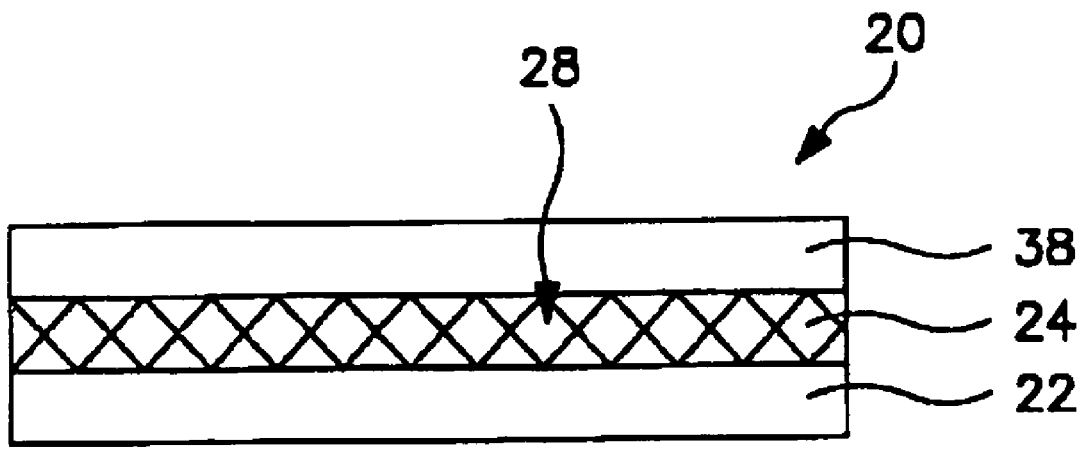
FIGS. 5-7 are enlarged cross-sectional views of other embodiments of a stretchable laminate.

In one embodiment, illustrated in FIG. 5 for example, the laminate 20 may include an extendable film layer 22, filled with calcium carbonate or other suitable filler to provide breathability upon stretching. The laminate 20 may also include an inherently extendable or elastic nonwoven facing layer 38, such as a bicomponent spunbond web, or adhesively laminated layers of such materials. Between the film layer 22 and the nonwoven facing layer 38 is an extruded layer of elastomeric openwork 24 in the form of an elastomeric mesh structure 28, which can be made with an elastomer and can also provide bias stretch due to the structure. This laminate 20 has the advantage of using a film layer 22 that can be formulated to meet breathability targets without the additional burden of being elastic by essentially decoupling elastic and breathability requirements for the film layer 22. The elastomeric mesh structure 28 is essentially an extruded layer so there is flexibility in resin choice, mesh structure, and the like.

Figure 6:
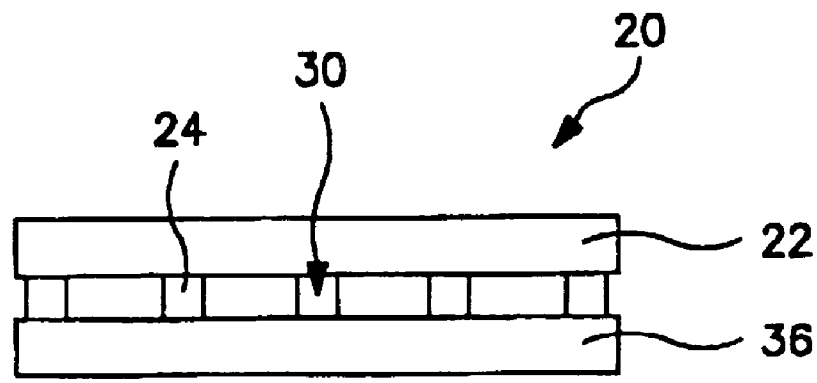

In another embodiment, illustrated in FIG. 6 for example, the laminate 20 may include a breathable cross-direction-extendable film layer 22, or a very low basis weight monolithic film layer 22, with a layer of elastomeric openwork 24 in the form of an elastomer 30 printed onto a surface of the film layer 22 in stripes or bars. The printed elastomer 30 provides sufficient stretch and recovery. The film layer 22 is then laminated to an inherently extendable and/or elastic film layer 36 with the printed elastomer 30 positioned between the two film layers 22, 36.

Figure 7:
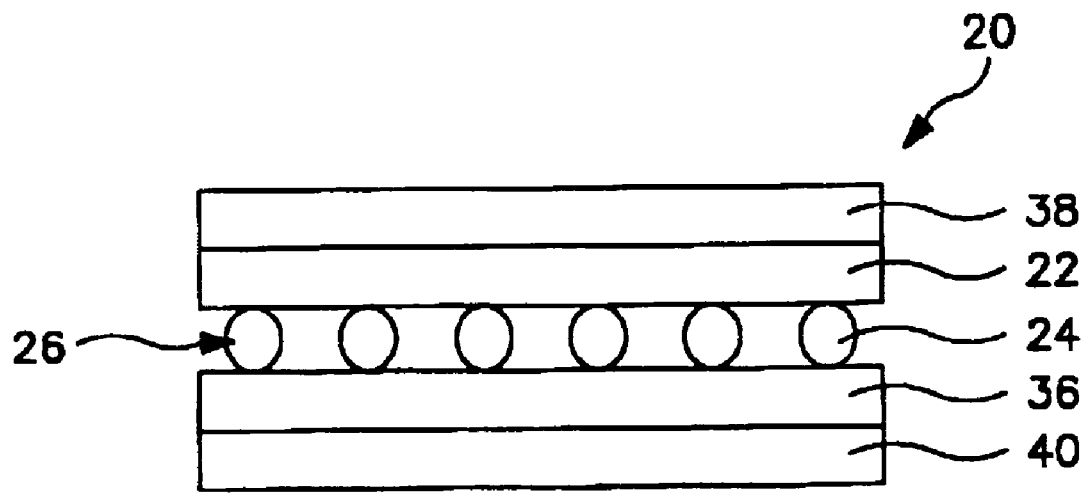

In yet another embodiment, illustrated in FIG. 7 for example, the laminate 20 may include two outer film layers 22, 36 that are breathable and extendable or elastic, and a layer of elastomeric openwork 24 in the form of elastic strands 26 between the two outer film layers 22, 36. Each of the film layers 22, 36 and the elastomeric openwork 24 is extruded through a die, with the elastomeric openwork 24 extruded through a die designed to create strips or ribbons of elastomer. Facing layers 38, 40 are either adhesively or thermally bonded to the outer film layers 22, 36.

Figure 8:
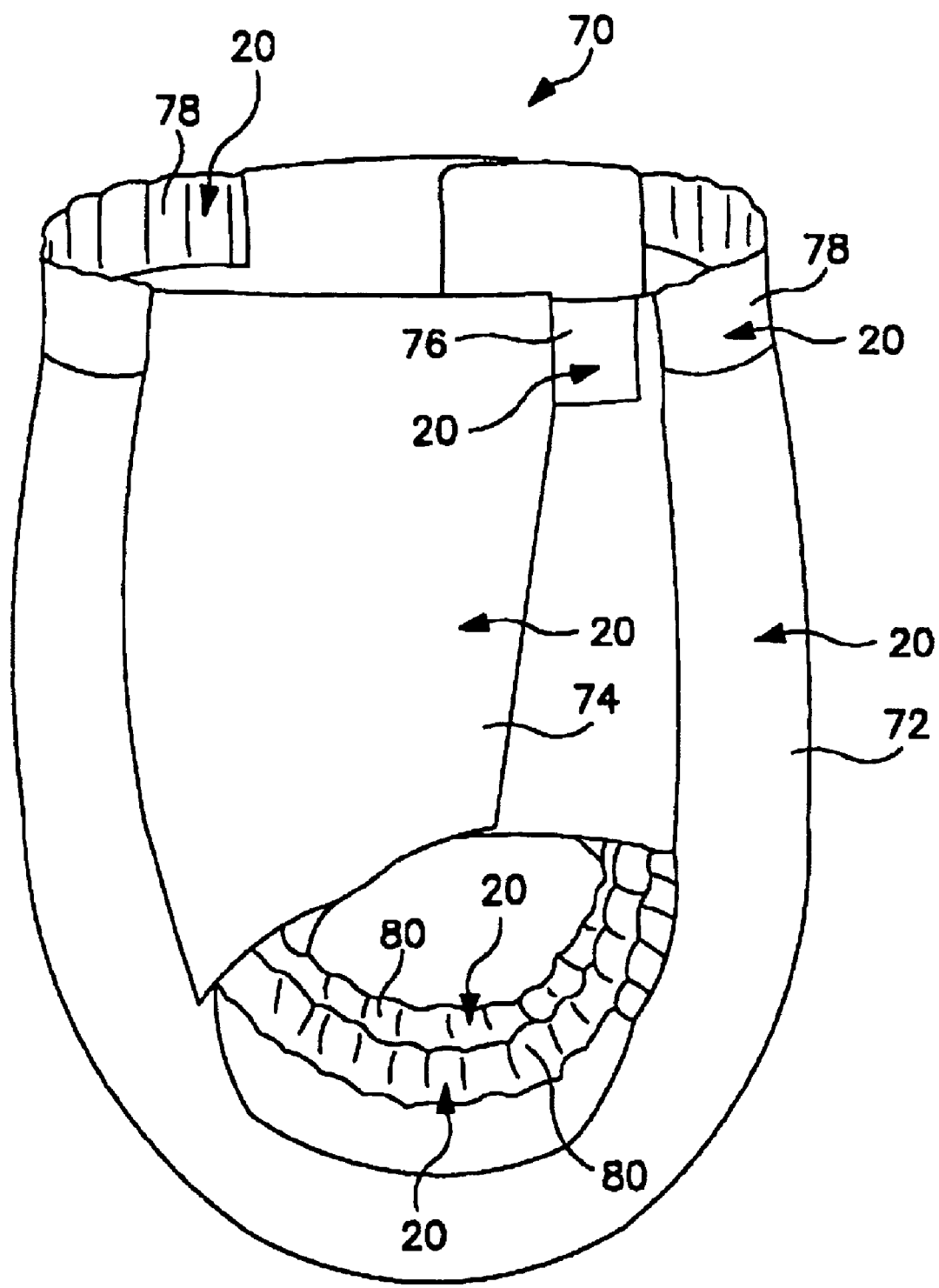
FIG. 8 is a perspective view of a garment including stretchable laminates in various locations.

The stretchable laminates 20 are particularly useful in providing stretch characteristics in personal care absorbent garments 70, as shown in FIG. 8. More specifically, as shown in FIG. 8, the stretchable laminates 20 are particularly suitable for use in providing outer covers 72 with breathability, cross-direction extensibility, and possibly dampness control. Additionally, the stretchable laminates 20 are also particularly suitable for use in side panels 74, ears 76, waistbands 78, and/or leg elastics 80 in such garments.

Figure 9:
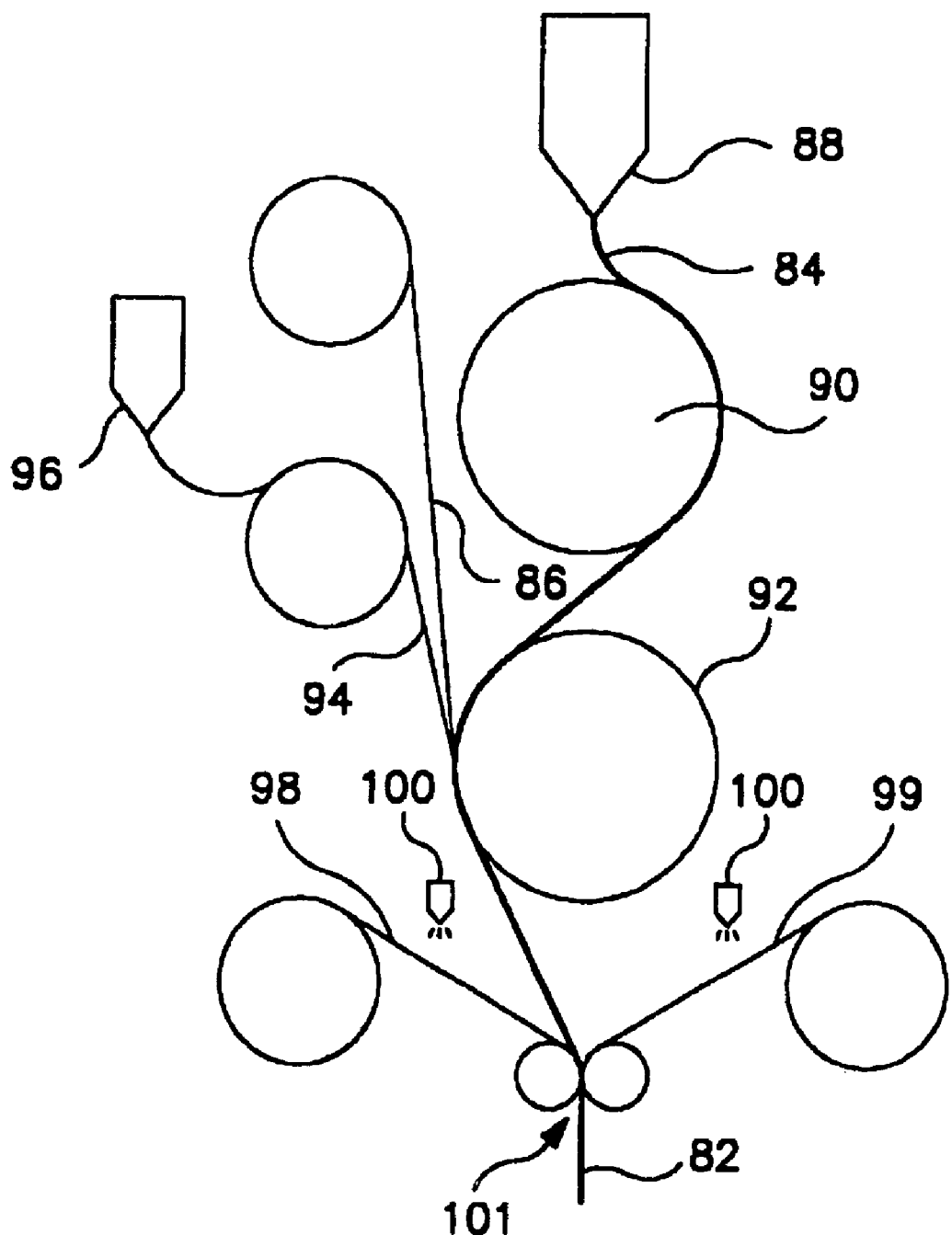
FIG. 9 is a schematic view of one embodiment of a method of making a stretchable laminate.

FIG. 9 illustrates a method and apparatus for making a stretchable laminate 82 as described above. As shown, a film 84 is extruded from a first film die 88, suitably onto a first roll 90. The first roll 90 may be temperature-adjustable, such as a warming roll or a chill roll. The film 84 is stretched between the first roll 90 and a second roll 92 as the film 84 is conveyed toward a nip 101. A layer of elastomeric openwork 86, as described above, may be formed and stretched as the elastomeric openwork 86 is conveyed onto the film 84.

The method may also include thinning, necking, and/or heat-treating the film 84. The film 84 may also be stretched a second time, particularly after cooling. The elastomeric openwork 86 may also be heat-treated and/or stretched a second time. Alternatively, ribbons of film rather than the elastomeric openwork 86 may be stretched and adhered to the stretched film 84. As another alternative, both ribbons of film 94 and the elastomeric openwork 86 may be adhered to the film 84. The stretching steps create thinner films 84 or thinner elastomeric openwork 86, resulting in laminates 82 that are thinner overall.

Optionally, a second film 94 may be cast through a second film die 96 over the elastomeric openwork 86 on top of the first film 84 as the first film is stretched, thereby encapsulating the elastomeric openwork 86 between film layers 84, 94. The first film 84 and/or the second film 94 may instead be a foam, or a foamed elastomer, that is foamed inline. Polyurethane film does not set up right away and would therefore foam easily. Alternatively, the first film 84 and/or the second film 94 may be in the form of film ribbons, as described above. Like the first film 84, the second film 94 may also be thinned, necked, and/or heat-treated.

Additionally, one or more facing layers 98, 99 may be bonded to the film 84 and/or 94, and/or the elastomeric openwork 86. The facing layer(s) may include any of the previously discussed facing layer materials, such as a necked material. Various post treatments, such as treatment with grooved rolls, which alter the mechanical properties of the facing layers 98, 99, are also suitable for use. The facing layers 98, 99 might also be made in situ rather than unrolled from previously-made rolls of material.

The laminate 82 resulting from this embodiment of the method may have different stretch in the machine direction than in the cross direction. Furthermore, the laminates may be "zoned," with different elastic properties along the length and/or width of the laminate, which may be created through zoning the first film 84, the elastomeric openwork 86, and/or the second film 94. Additionally, adhesive 100 used to bond the facing layers 98, 99 to the film 84, 94 may be zoned to create additional functionality.

Figure 10:
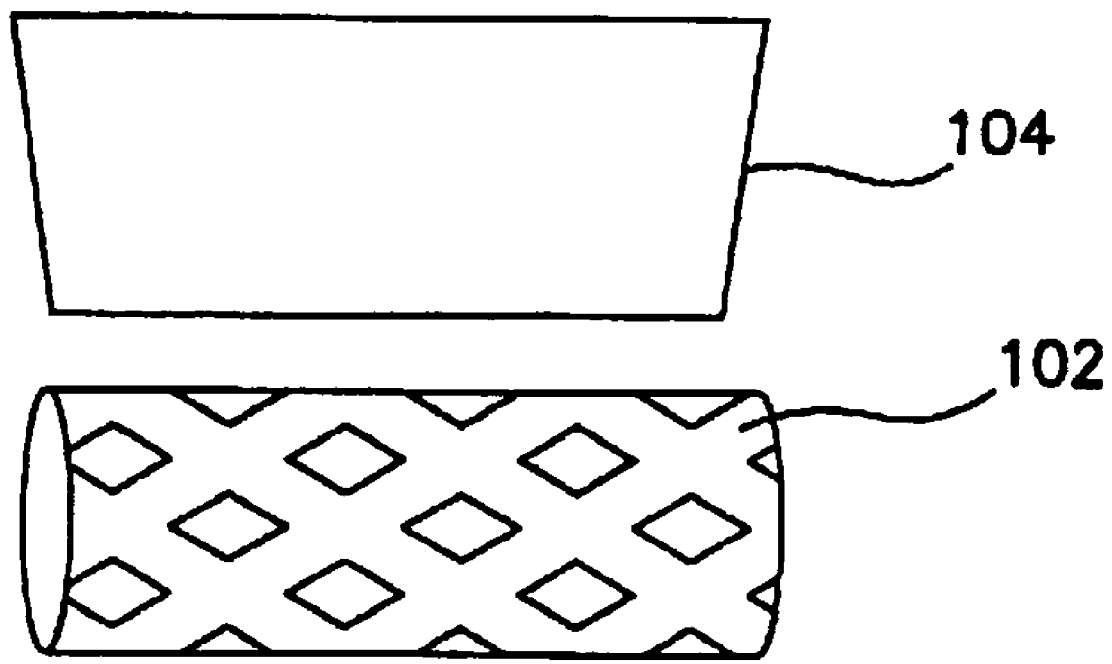
FIG. 10 is a schematic view of a lattice-design roller that can be used to produce an elastomeric mesh structure.

The film 84, 94 in this method may be any of the suitable types of film described in detail above, including elastomeric films, foamed elastomers, filled films, and elastomeric adhesive films. Also, the elastomeric openwork 86 may be in the form of elastic strands, an elastomeric mesh structure, or any other suitable form, as described in detail above. An illustration of apparatus suitable for creating an elastomeric mesh structure is provided in FIG. 10. More particularly, the apparatus includes a patterned roll 102 onto which the elastomer is extruded from a film die 104.

Most laminates currently have one layer of elastomeric material or at most two that are integrated upon extrusion and not handled separately green before they are integrated together. As used herein, the term "green" refers to a material that has never been rolled up or otherwise placed in storage. For example, the laminate is produced within 5 minutes, 3 minutes, 1 minute, 30 seconds, 15 seconds, or 5 seconds of production of the "green" material. The ability to handle the film 84, 94 and elastomeric openwork 86 separately, but in the same process, provides benefits to forming new elastic structures beyond those currently practiced.

By fixing the elastomeric openwork 86 onto the green film 84 the occurrence of strand or mesh slippage is greatly reduced. Since the film 84 is pressure-sensitive and tacky when the elastomeric openwork 86 is applied to the film 84, the need for adhesive between the film 84 and the elastomeric openwork 86 is eliminated, and, in addition, strand or mesh slippage is prevented. Additionally, the elastomeric openwork 86 may be at least partially embedded in, or encapsulated by, the layer of green film 84.

Another advantage of this method is that the first and second rolls 90, 92, which can serve as cast and annealing rolls, respectively, can be run independent of each other in terms of temperature and speed, which means that the film 84 can be annealed or cooled as desired to introduce properties such as latency, deadening of the elastic, or even enhancing the setting of the elastomer for more immediate elastic properties.

The resulting laminates 82 may have a multi-phase stretchability profile. As used herein, the term "multi-phase stretchability profile" refers to a laminate or other composite that demonstrates a change in extension modulus, such that an elongation-versus-tension profile of the laminate depicts three or more distinct stretchability phases that correspond to at least three different layers having different elongation-versus-tension profiles within the laminate. Laminates having a multi-phase stretchability profile have unique stretch characteristics, such as multiple stretch-to-stop values at certain tensioning forces.

Figure 11A:
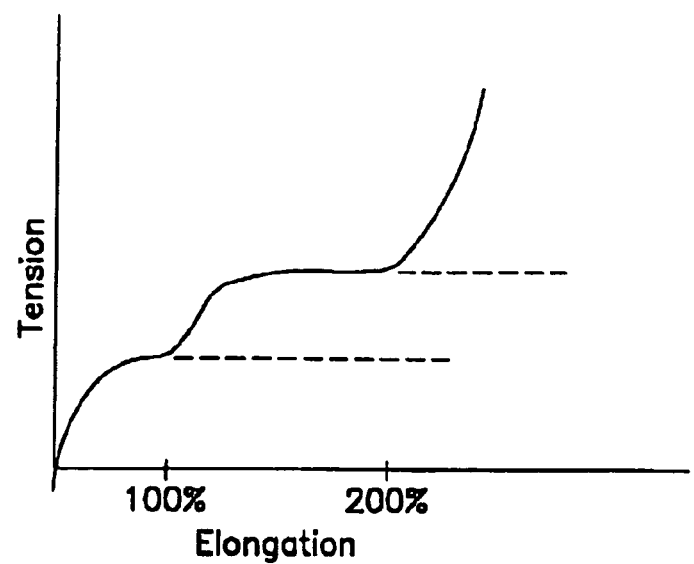
FIG. 11a is an elongation-versus-tension profile of a laminate having a multi-phase stretchability profile.
Figure 11B:
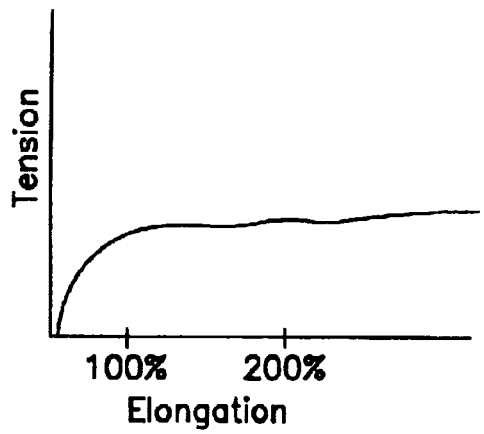
Figure 11C:
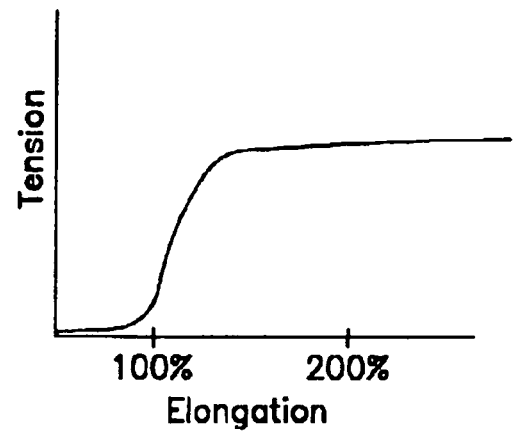
Figure 11D:
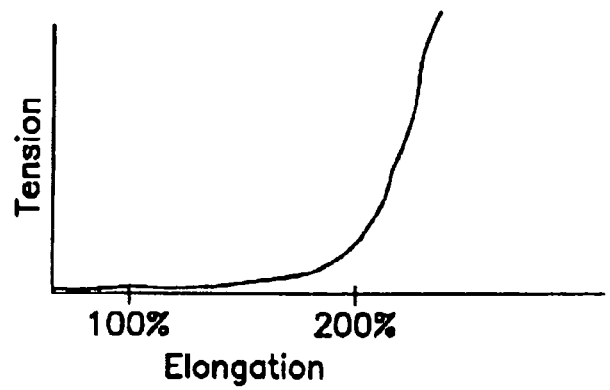

For example, FIG. 11a is an exemplary elongation-versus-tension profile of a laminate having a multi-phase stretchability profile in the machine direction. The particular laminate having the multi-phase stretchability profile illustrated in FIG. 11a may include a film layer 84 that is stretched by about 200% in the machine direction and a layer of elastomeric openwork 86 that is stretched by about 100% in the machine direction when the film layer 84 and the elastomeric openwork 86 are bonded together. One or more facings 98, 99 may then be bonded to the stretched film layer 84 and the stretched elastomeric openwork 86, both of which are still stretched by their respective amounts of 200% and 100% in the machine direction. After passing through the nip 101, the laminate 82 may be relaxed. Upon relaxation, the facings 98, 99 would retract by about 200% due to contraction of the stretched film layer 84. Similarly, the elastomeric openwork 86 would retract by about 100% due to relaxation of the stretched film layer 84. FIG. 11b is an exemplary elongation-versus-tension profile of the film layer 84 within the laminate. The film layer 84 initially exhibits an increase in tension with the increase of elongation, but the tension levels off around 100% elongation. FIG. 11c is an exemplary elongation-versus-tension profile of the elastomeric openwork 86 within the laminate. Because the elastomeric openwork 86 is gathered due to the 100% retraction, essentially no tension occurs during the first 100% elongation; however, once the elastomeric openwork 86 is ungathered (at 100% elongation), the tension increases with the increase of elongation and levels off around 200% elongation. FIG. 11d is an exemplary elongation-versus-tension profile of the facings 98, 99 within the laminate. Because the facings 98, 99 are gathered due to the 200% retraction, essentially no tension occurs during the first 200% elongation; however, once the facings 98, 99 are ungathered (at 200% elongation), the tension increases at a rapid rate. In FIG. 11a it can be seen that the laminate 82 as a whole displays the three phases of the three different types of layers separately. The resulting laminate 82 thus has machine direction stretchability of over 200%. If the facings 98, 99 are necked, the laminate 82 may also have cross direction stretchability.

Figure 12A:
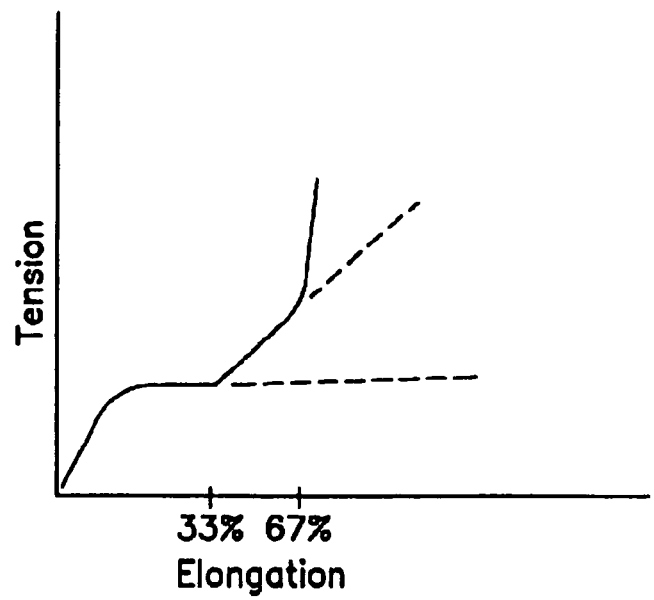
FIG. 12a is an elongation-versus-tension profile of another laminate having a multi-phase stretchability profile.
Figure 12B:
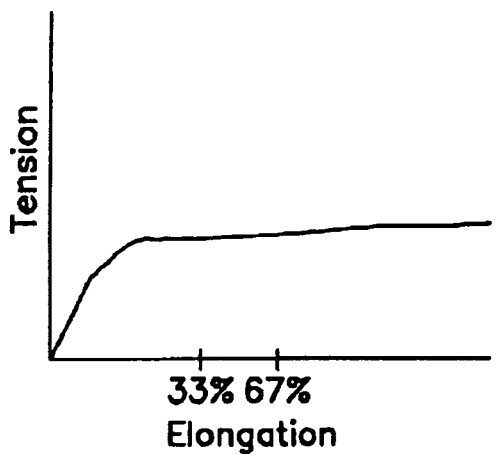
Figure 12C:
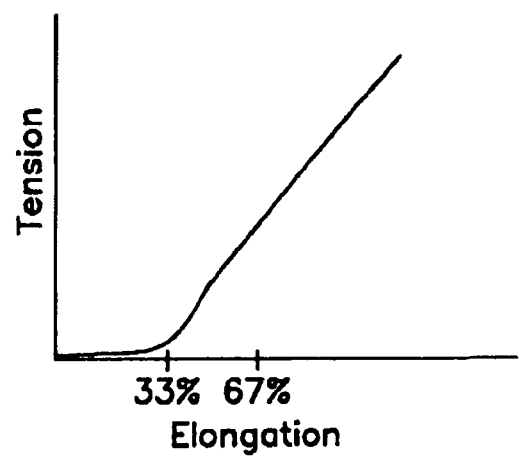
Figure 12D:
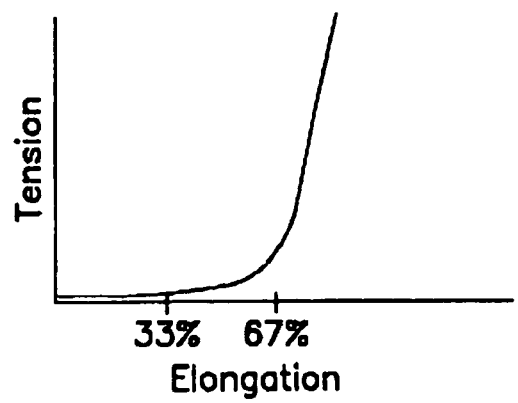

An exemplary elongation-versus-tension profile of another laminate having a multi-phase stretchability profile in the cross direction is illustrated in FIG. 12a. The particular laminate having the multi-phase stretchability profile illustrated in FIG. 12a may include a film layer 84 (or a layer of elastomeric openwork 86) bonded to a first facing 98 that is necked by about 25% and to a second facing 99 that is necked by about 40%. Elongating the resulting laminate 82 in the cross direction would result in the elongation-versus-tension profile of FIG. 12a. FIG. 12b is an exemplary elongation-versus-tension profile of the film layer 84 within the laminate. The film layer 84 initially exhibits an increase in tension with the increase of elongation, but the tension levels off at less than 33% elongation. FIG. 12c is an exemplary elongation-versus-tension profile of the first facing 98 within the laminate. Because the first facing 98 is necked by about 25%, the first facing 98 reaches its unnecked width when the laminate is stretched by about 33%, at which point the tension drastically increases. FIG. 12d is an exemplary elongation-versus-tension profile of the second facing 99 within the laminate. Because the second facing 99 is necked by about 40%, the second facing 98 reaches its unnecked width when the laminate is stretched by about 67%, at which point the tension drastically increases. In FIG. 12a it can be seen that the laminate 82 as a whole displays the three phases of the three different types of layers separately. The resulting laminate 82 thus has cross direction stretchability of about 67%.

Figure 13A:
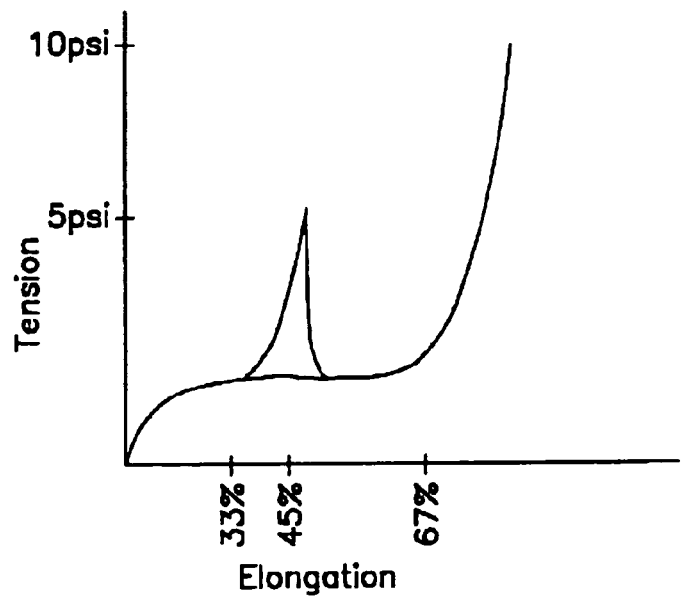
FIG. 13a is an elongation-versus-tension profile of yet another laminate having a multi-phase stretchability profile.
Figure 13B:
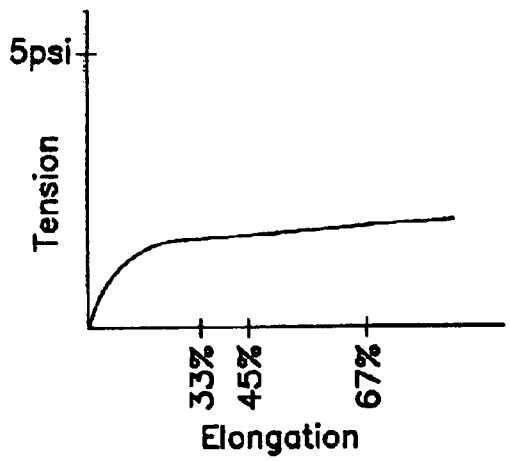
Figure 13C:
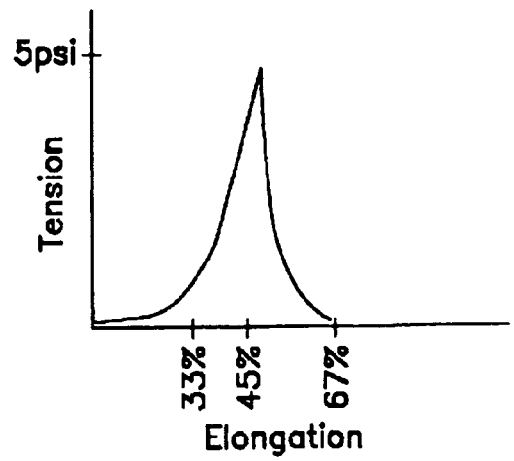
Figure 13D:
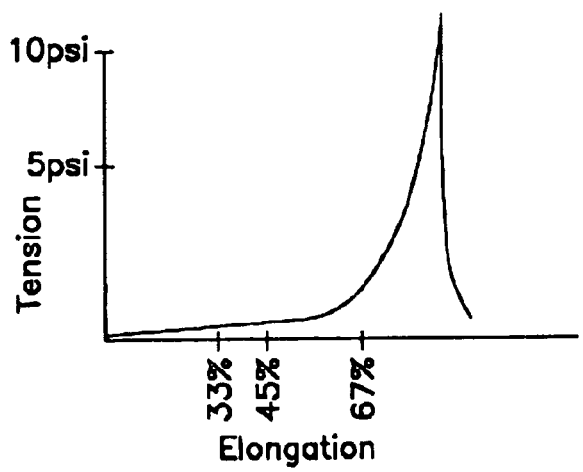

An exemplary elongation-versus-tension profile of yet another laminate having a multi-phase stretchability profile in the cross direction is illustrated in FIG. 13a. The particular laminate having the multi-phase stretchability profile illustrated in FIG. 13a may include a film layer 84 (or a layer of elastomeric openwork 86) bonded to a first facing 98 of relatively weak material that is necked by about 25% and to a second facing 99 of stronger material that is necked by about 40%. Elongating the resulting laminate 82 in the cross direction would result in the elongation-versus-tension profile of FIG. 13a. FIG. 13b is an exemplary elongation-versus-tension profile of the film layer 84 within the laminate. The film layer 84 initially exhibits an increase in tension with the increase of elongation, but the tension levels off at less than 33% elongation. FIG. 13c is an exemplary elongation-versus-tension profile of the first facing 98 within the laminate. Because the first facing 98 is necked by about 25%, the first facing 98 reaches its unnecked width when the laminate is stretched by about 33%, at which point the tension drastically increases; however, when the tension exceeds the material's strength, such as around 5 psi, the first facing 98 tears or otherwise fails. FIG. 13d is an exemplary elongation-versus-tension profile of the second facing 99 within the laminate. Because the second facing 99 is necked by about 40%, the second facing 98 reaches its unnecked width when the laminate is stretched by about 67%, at which point the tension drastically increases. Since the second facing 99 is stronger than the first facing 98, the second facing 99 enables the laminate to withstand greater tension than the first facing 98 alone can withstand. In FIG. 13a it can be seen that the laminate 82 as a whole displays the three phases of the three different types of layers separately. In use, the failure of the first facing 98 at around 45% cross direction stretch may serve as a warning sign to a user that the laminate is approaching a peak tension load, thereby signaling to the user that no additional tension should be applied to the laminate in order to avoid laminate failure. Despite the failure of the first facing 98, the laminate may be capable of stretching over 67% in the cross direction without resulting in failure of the second facing 99.

In another embodiment of the invention, a machine 105 capable of carrying out both vertical filament laminate (VFL) processes and neck bonded laminate (NBL) processes can be used to carry out any of the methods of the invention. This machine 105 has unique characteristics that allow it to process machine direction, cross direction and bi-axial stretch materials.

Both NBL and VFL laminates may include similar facing materials, such as spunbond or other suitable nonwoven webs, with the facing materials in the NBL being neck-stretched. Furthermore, the facing materials in both the NBL and VFL processes may be adhesively or thermally bonded to an elastic core. The elastic core may be a layer of elastomeric openwork, as described above. More particularly, the elastic core may be either a cast film for NBL or filament strands for VFL, for example.

Figure 14:
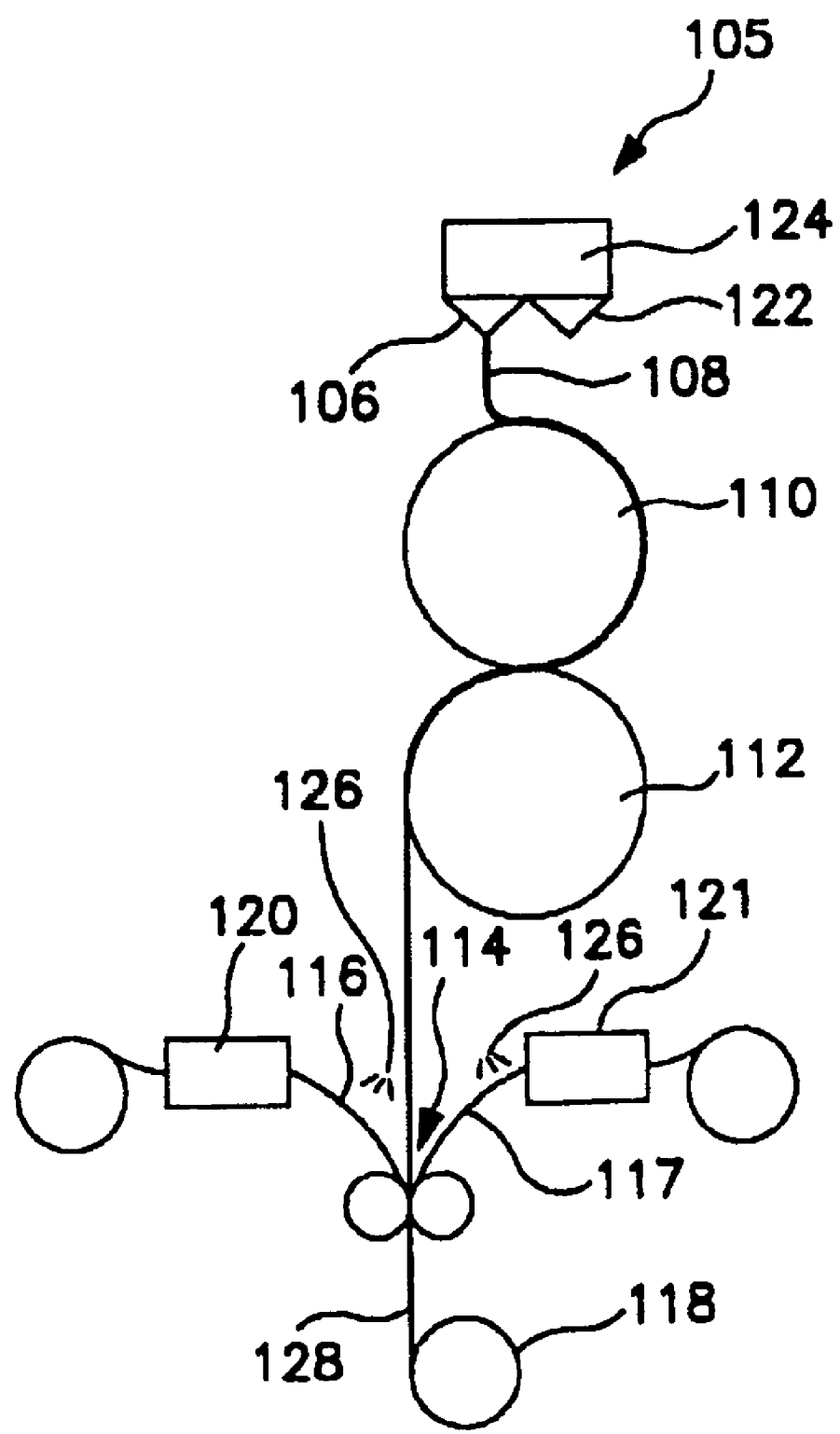
FIG. 14 is a schematic view of one embodiment of a machine that can produce machine-direction, cross-direction, and biaxial stretch materials.

One embodiment of the combination machine 105 is illustrated in FIG. 14. The machine 105 is based on a conventional VFL platform including a filament die 106 for extruding the elastic core 108 from an extruder 124 onto a first roll or forming roll 110, and a second roll 112 which passes the elastic core 108 downstream to a nip 114 with the facings 116, 117 applied to the elastic core 108 prior to passing through the nip 114 and onto a winder 118. One or both of the rolls 110, 112 may be a chill roll. One or more adhesive application zones 126 may be present in the machine upstream of the nip 114. Downstream of the nip 114, such as in the space between the nip 114 and the winder 118, there may be a relaxation zone 128 having negligible tension.

Additional equipment is added to the VFL platform to enable the production of NBL. The additional equipment includes one or more ovens 120, 121 for neckstretching the facings 116, 117 and a film die 122 mounted adjacent to the filament die 106. The similar throughputs of NBL and VFL, based on elastic basis weight and web width, enable the two processes to be combined into one machine while utilizing the same extruder 124 and pellet handling systems, or alternatively, conventional hot-melt equipment such as a melt tank or an extruder. As another alternative, the film die 122 and the filament die 106 may be fed from different extruders.

Figure 15:
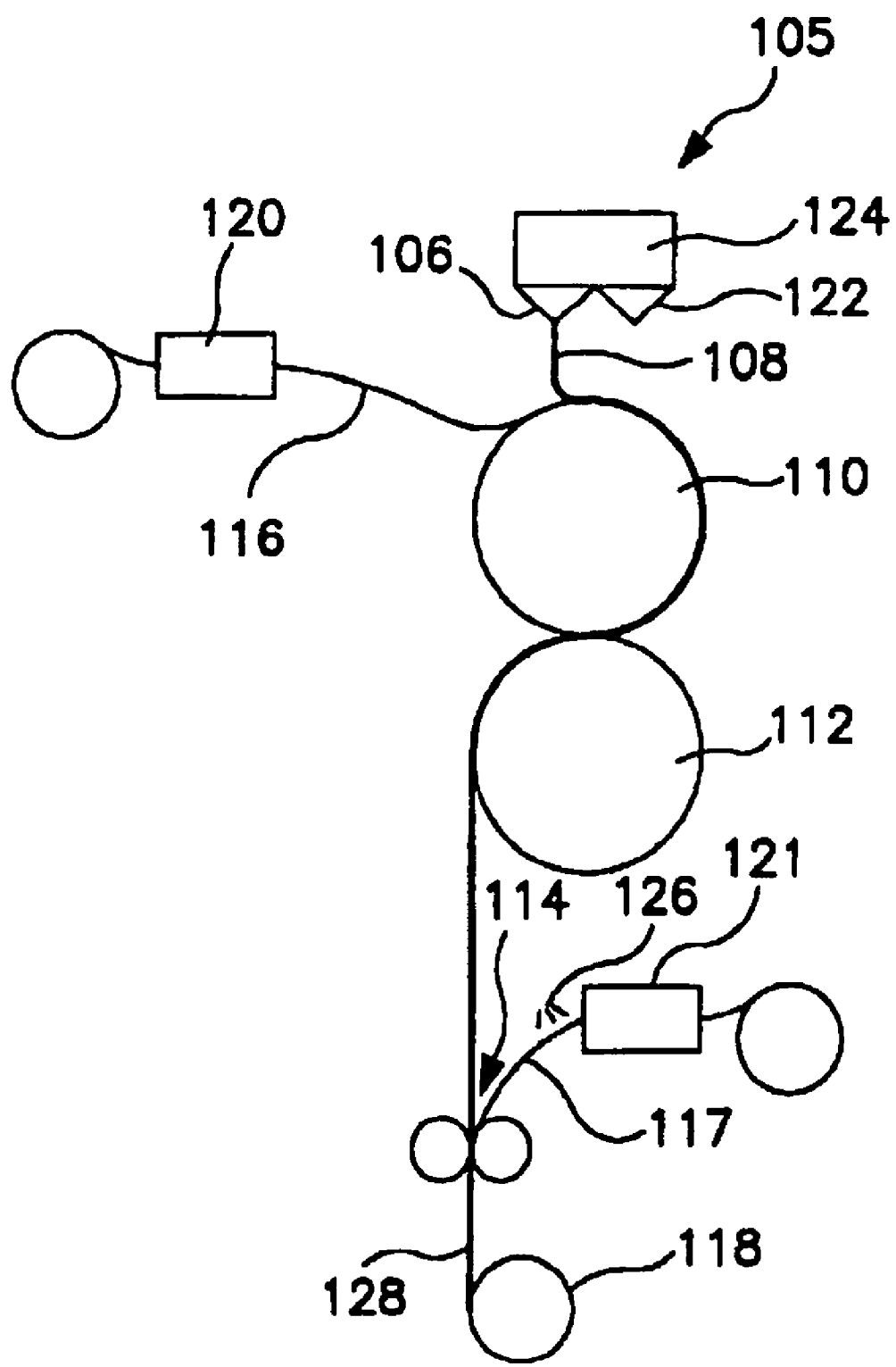
FIG. 15 is a schematic view of another embodiment of a machine that can produce machine-direction, cross-direction, and biaxial stretch materials.

Alternatively, the machine 105 may be set up such that one of the facings 116 is guided onto the first forming roll 110 and the elastic core 108 is extruded onto the facing 116. This embodiment of the machine is illustrated in FIG. 15.

As yet another embodiment, rather than being unwound from a roll, one or more of the facings 116, 117 may be formed simultaneously through additional extruders.

The elements of each embodiment disclosed herein are readily interchangeable with, or can be combined with, the other embodiments.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A stretchable laminate, comprising:
    a first elastic film layer;
    a second layer; and
    an elastomeric openwork layer bonded to the first and second layers;
    wherein the elastomeric openwork layer is selected from the group consisting of a plurality of parallel elastic strands, an elastomer printed in a pattern on the first layer, and combinations thereof, and the laminate has a multi-phase stretchability profile including first, second and third successive and distinct stretchability phases at progressively higher elongations, the second phase exhibits consistently higher tension than the first phase, and the third phase exhibits consistently higher tension than the second phase.

2. The stretchable laminate of claim 1, wherein the laminate has a multi-phase stretchability profile in a machine direction.

3. The stretchable laminate of claim 1, wherein the laminate has a multi-phase stretchability profile in a cross direction.

4. The stretchable laminate of claim 1, wherein the second layer is selected from the group consisting of a necked material, a nonwoven web, a film, a spunbond web, a meltblown web, and combinations thereof.

5. The stretchable laminate of claim 1, wherein the first and second layers are both necked, and the first layer is necked to a greater extent than the second layer.

6. The stretchable laminate of claim 1, wherein the first layer can withstand greater tension without failure than the second layer.

7. The stretchable laminate of claim 1, wherein the second layer is elastomeric.

8. The stretchable laminate of claim 1, wherein the elastomeric strands are zoned.

9. The stretchable laminate of claim 1, wherein the laminate is incorporated into a garment in at least one of the group consisting of side panels, ears, waistbands, leg elastics, outer covers, and combinations thereof.

10. The stretchable layer of claim 1, wherein the second layer comprises a film which includes a filler and is liquid-impermeable and water vapor transmissible.

11. The stretchable laminate of claim 1, wherein the first elastic film layer comprises a multilayer material.

12. The stretchable laminate of claim 1, wherein the first elastic film comprises a foamed material.

13. The stretchable laminate of claim 1, wherein the second layer comprises a film layer.

14. The stretchable laminate of claim 13, wherein the first and second layers comprise the same material.

15. The stretchable laminate of claim 13, wherein the second layer comprises a plurality of ribbons.

16. The stretchable laminate of claim 15, wherein the ribbons are zoned to create regions of higher and lower tension.

17. The stretchable laminate of claim 1, further comprising a nonwoven facing layer.

18. The stretchable laminate of claim 1, further comprising first and second nonwoven facing layers.

19. The stretchable laminate of claim 17, wherein the nonwoven facing layer comprises a necked material.

20. The stretchable laminate of claim 1, wherein the elastomeric openwork layer is zoned.

21. The stretchable laminate of claim 1, wherein the laminate is zoned.

22. The laminate of claim 1, wherein each of said layers has a different elongation-versus-tension profile within the laminate.

23. A stretchable laminate, comprising:
a first layer;
a second layer; and
an elastomeric openwork layer bonded to the first and second layers;
wherein the elastomeric openwork layer is selected from the group consisting of a plurality of parallel elastic strands, an elastomer printed in a pattern on the first layer, and combinations thereof, and the laminate has a multi-phase stretchability profile including first, second and third successive and distinct stretchability phases at progressively higher elongations, the second phase exhibits consistently higher tension than the first phase, and the third phase exhibits consistently higher tension than the second phase.

* * * * *